United States Patent
Thai-Van et al.

(10) Patent No.: US 10,299,696 B2
(45) Date of Patent: May 28, 2019

(54) ELECTROPHYSIOLOGICAL METHOD FOR ASSESSING THE EFFECTIVENESS OF A HEARING AID

(71) Applicants: HOSPICES CIVILS DE LYON, Lyons (FR); UNIVERSITE CLAUDE BERNARD LYON 1, Villeurbanne (FR)

(72) Inventors: Hung Thai-Van, Lyons (FR); Anne Caclin, Serezin de la Tour (FR); Ludovic Bellier, Lyons (FR); Jean-Francois Vesson, Francheville (FR); Evelyne Veuillet, Lyons (FR)

(73) Assignees: HOSPICES CIVILS DE LYON, Lyons (FR); UNIVERSITE CLAUDE BERNARD LYON 1, Villeurbanne (FR)

( * ) Notice: Subject to any disclaimer, the term of this patent is extended or adjusted under 35 U.S.C. 154(b) by 299 days.

(21) Appl. No.: 15/030,673

(22) PCT Filed: Oct. 24, 2014

(86) PCT No.: PCT/FR2014/052711
§ 371 (c)(1),
(2) Date: Apr. 20, 2016

(87) PCT Pub. No.: WO2015/059425
PCT Pub. Date: Apr. 30, 2015

(65) Prior Publication Data
US 2016/0262651 A1 Sep. 15, 2016

(30) Foreign Application Priority Data

Oct. 25, 2013 (FR) ..................... 13 60447

(51) Int. Cl.
*A61B 5/0484* (2006.01)
*A61B 5/04* (2006.01)
(Continued)

(52) U.S. Cl.
CPC ........ *A61B 5/04845* (2013.01); *A61B 5/0006* (2013.01); *A61B 5/048* (2013.01);
(Continued)

(58) Field of Classification Search
None
See application file for complete search history.

(56) References Cited

U.S. PATENT DOCUMENTS

| 8,014,853 B2 | 9/2011 | Kraus et al. |
| 2012/0130449 A1* | 5/2012 | Carlyon ............... A61N 1/0541 607/57 |

FOREIGN PATENT DOCUMENTS

WO 2013/017169 2/2013

OTHER PUBLICATIONS

Harvey Dillon, "So, baby, how . . . with hearing aids", The Hearing Journal, vol. 58, No. 10, Oct. 1, 2005, pp. 10-17.
(Continued)

*Primary Examiner* — Brian T Gedeon
(74) *Attorney, Agent, or Firm* — Clark & Brody

(57) ABSTRACT

A method of evaluating the effectiveness of an auditory prosthesis comprises transmitting a stimulus via an auditory prosthesis, thereby delivering an auditory stimulus to the auditory nervous system of a person fitted with said auditory prosthesis, picking up the neurophysiological signals transmitted by said auditory nervous system in response to the auditory stimulus by means of an electro- or magneto-encephalography system, and processing the received signals. The method also includes transmitting a stimulus made up of at least one pair of linguistic units selected from a
(Continued)

phonetic confusion matrix, picking up a neurophysiological signal in response separately for each linguistic unit, and comparing the signals in order to evaluate the effectiveness of the prosthesis.

4 Claims, 8 Drawing Sheets

(51) Int. Cl.
    *A61B 5/048*     (2006.01)
    *A61B 5/00*     (2006.01)
    *A61B 5/12*     (2006.01)
    *H04R 25/00*     (2006.01)

(52) U.S. Cl.
    CPC ...... *A61B 5/04009* (2013.01); *A61B 5/04012* (2013.01); *A61B 5/125* (2013.01); *A61B 5/4836* (2013.01); *A61B 5/4851* (2013.01); *A61B 5/7246* (2013.01); *H04R 25/70* (2013.01)

(56) References Cited

OTHER PUBLICATIONS

Kraus et al., "The mismatch negativity . . . in cochlear-implant users", Hearing Research, Elsevier Science Publishers, vol. 65, No. 1-2, Feb. 1, 1993, pp. 118-124.

\* cited by examiner

| | | | |
|---|---|---|---|
| mop | ma | bike | buy |
| rope | row | lock | law |
| pipe | pie | rock | raw |
| pop | pa | rake | ray |
| boat | bow | moon | moo |
| note | know | rain | ray |
| boot | boo | bone | bow |
| bait | bay | bean | bee |
| beet | bee | | |
| | | | |
| car | tar | lock | walk |
| key | tea | lake | wake |
| kick | tick | line | whine |
| cake | take | rock | walk |
| cook | took | rake | wake |
| comb | tome | rag | wag |
| cap | tap | red | wed |
| core | tore | | |
| | | | |
| spot | pot | smash | mash |
| spur | purr | snow | know |
| speck | peck | snail | nail |
| spike | pike | sneeze | knees |
| spy | pie | snap | nap |
| spill | pill | school | cool |
| store | tore | ski | key |
| stick | tick | scar | car |
| stop | top | scoop | coop |
| star | tar | sled | lead |
| stair | tear | slime | lime |
| stool | tool | slip | lip |
| smile | mile | swing | wing |
| small | mall | sweep | weep |
| smack | mack | sweater | wetter |

FIG.5

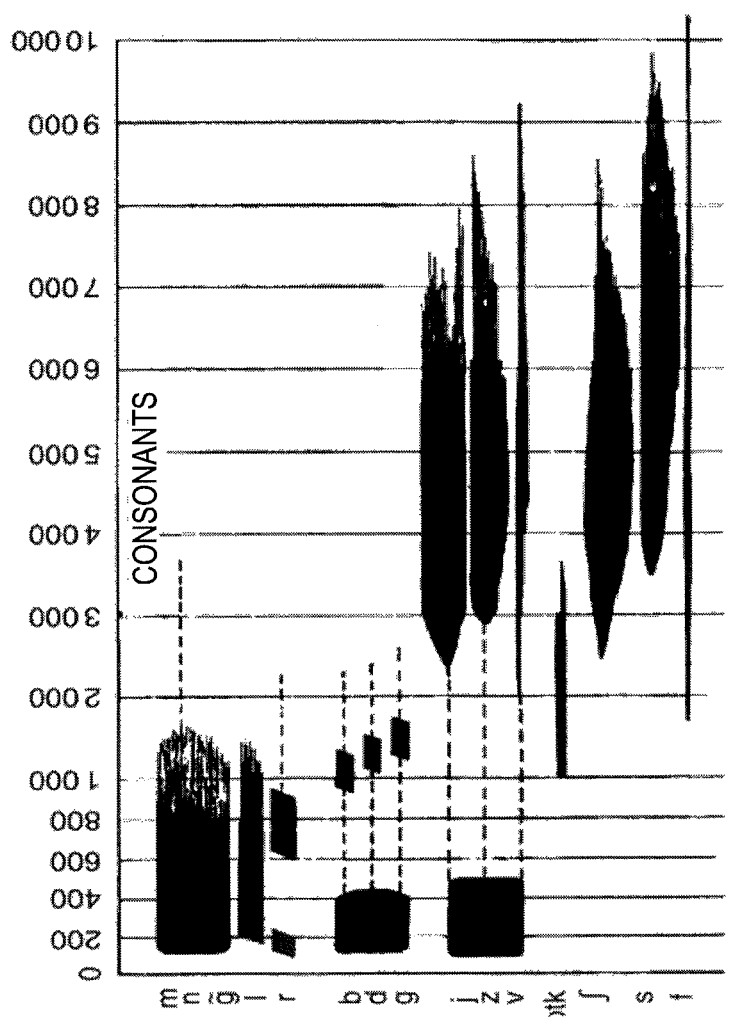

ELECTROPHYSIOLOGICAL METHOD FOR ASSESSING THE EFFECTIVENESS OF A HEARING AID

The present invention relates to the technical field of evaluating auditory prostheses. The invention relates firstly to external auditory prostheses such as traditional Behind-the-Ear (BTE) hearing aids, slim-tubing BTE hearing aids (e.g. "Life Tubes"), Receiver-in-the-Canal (RIC) hearing aids, intra-auricular hearing aids, or spectacle hearing aids. The invention also relates to prostheses that are totally or partially implanted, such as bone anchored implants, semi- or totally implantable middle ear implants (with air conduction or bone conduction), cochlear implants, electro-acoustic cochlear implants, or brainstem implants.

Deafness is a pathological condition characterized by partial or total loss of the sense of hearing, and the prosthesis sets out to mitigate that loss of the sense of hearing.

At present, in clinical practice, auditory correction systems are adjusted in order to improve the understanding of speech on the basis of subjective tests that require active participation from the hard-of-hearing subject (pure-tone and speech audiometry) and on the expertise of the audio prosthetist. Given that the auditory prostheses that are available on the market are biomedical devices that are expensive, and given the impact of deafness on ability to communicate and socialize at all ages in life, it is becoming crucial to be able to adjust auditory prostheses in optimum manner in order to guarantee the best possible therapeutic compliance. In particular, situations exist in which the reliability and the reproducibility of subjective testing raise difficulties (extreme ages: infants and senior citizens, associated handicaps, e.g. trisomy 21) for which recourse to an objective method of adjusting and monitoring the auditory equipment needs to be recommended. At present, when not wearing an auditory prosthesis, electrophysiological measurements enable the auditory function to be evaluated objectively in routine clinical manner.

In conventional manner, in response to a speech stimulus, two types of response are distinguished:
- high-frequency responses (above about 80 hertz (Hz)), of origin that is assumed to be sub-cortical (coming in particular from the brainstem), and thus generally referred to in the literature as speech auditory brainstem response ("speech ABR"). The physical characteristics of speech ABRs serve not only to verify that the delivered speech sound is detected by the auditory nervous system, but also that it is properly coded and that the coding enables the auditory nervous system to discriminate it from another speech sound; and
- low-frequency responses (below about 80 Hz), of origin that is assumed to be essentially cortical. These responses are generally labeled by their sign and by the latency in milliseconds at the vertex: P50, N100, P200, etc.

For a subject wearing an auditory prosthesis, patent application WO 2008/116462 describes a system for picking up electrophysiological responses to simple sounds (clicks, tone bursts), synthesized with a conventional electrical signal generator. The sounds are presented to an individual via the auditory prosthesis, and the system proposes solving the problem of synchronization between the acoustic signal and the neurophysiological system. Furthermore, the system claims the ability to test the auditory detection threshold made possible by wearing the prosthesis. Nevertheless, that patent application does not describe the use of language sounds as stimuli, nor does it describe improving the adjustment of the prosthesis on the basis of evaluating neurophysiological discrimination between speech sounds. Unfortunately, the ability to detect a sound does not mean that the subject has the ability to discriminate that sound from another sound that is similar but that presents an acoustic difference that is pertinent for the auditory central nervous system.

The document by Harvey Dillon "So, baby how does it sound? Cortical assessment of infants with hearing aids", The Hearing Journal, Vol. 58, No. 10, Oct. 1, 2005 (2005-10-01), pp. 10-17, XP055125165, ISSN: 0745-7472, DOI: 10.1097/.01.HJ.0000285781.30125.64 is an interview of a doctor describing a method seeking to adjust auditory prostheses for an infant. That method seeks to transmit a stimulus via the auditory prosthesis and to pick up the cortical auditory evoked potentials (AEPs). Measuring cortical responses does not provide information about how a sound is represented in the auditory nervous system in a manner that is sufficiently fine. Furthermore, the choice of stimulations proposed does not make it possible to assess the ability of a subject to discriminate between one sound and another sound that is similar, but that presents an acoustic difference that is pertinent for the auditory central nervous system.

The document by N. Kraus et al., "The mismatch negativity cortical evoked potential elicited by speech in cochlear-implant users", Hearing Research, Elsevier Science Publishers, Amsterdam, NL, Vol. 65, No. 1-2, Feb. 1, 1993 (1993-02-01), pp. 118-124, XP024397053, ISSN: 0378-5955, DO1: 10.1016/0378-59555(93)90206-G [extracted on 1993-02-01] describes a study seeking to show the existence of differentiation between two different sounds by the auditory system of patients having a cochlear implant. The method described seeks to pick up the cortical AEPs, so such a method does not provide sufficiently accurate information about the representation of a sound in the auditory nervous system.

For a subject not using an auditory prosthesis, U.S. Pat. No. 8,014,853 describes a system of picking up auditory electrophysiological responses of the brainstem to syllable type speech sounds [consonant-vowel] ("speech Auditory Brainstem Responses"). Those electrophysiological responses can then be analyzed and compared with a database of normative responses in order to assist in diagnosing difficulties of the auditory central nervous system in performing auditory processing. If such a difficulty is diagnosed, that invention makes it possible to give recommendations about a therapeutic intervention.

In this context, it becomes pertinent to seek to verify the quality of the neurophysiological processing of speech sounds by an individual wearing an auditory prosthesis, without necessarily having recourse to normative data. Specifically, in order for the processing of speech sounds by the auditory central nervous system to lead to good understanding of language, the key element is neither the exact form of the neurophysiological response to a given stimulation, nor any resemblance of that response to normative data. It is above all the ability of the central nervous system to process differently speech sounds that are acoustically similar so as to enable an individual wearing an auditory prosthesis to understand a speaker well.

The object of the invention is thus to propose an objective method for evaluating the effectiveness of an auditory prosthesis, on the assumption that the adjustment of the prosthesis should enable an individual wearing it to discriminate between the main acoustic traits of speech and thus to distinguish between at least two speech sounds that are acoustically similar.

Thus, the invention provides a method of evaluating the effectiveness of an auditory prosthesis, the method consisting:

in transmitting a stimulus via an auditory prosthesis, thereby delivering an auditory stimulus to the auditory nervous system of a person fitted with said auditory prosthesis;

in picking up the neurophysiological signals transmitted by said auditory nervous system in response to the auditory stimulus by means of an electro- or magneto-encephalography system; and in processing the received signals.

According to the invention, the method consists:

in transmitting a stimulus made up of at least one pair of linguistic units selected from a phonetic confusion matrix;

in picking up separately the electrophysiological signals in response to each linguistic unit administered via the auditory prosthesis; and in processing the signals:

by comparing the electrophysiological signals corresponding to the various tested linguistic units by performing one or more of the following steps consisting:

in extracting peak latencies, peak amplitudes, latency differences between peaks, slopes of the curve between two peaks, or areas under portions of the curve;

in searching in waveforms and/or in time-frequency decompositions for a response specifically expected for one of said linguistic units;

in directly comparing the waveforms of each neurophysiological signal picked up in response by subtraction; and in comparing the time-frequency decompositions; and by evaluating the effectiveness of the auditory prosthesis on the basis of the result of this comparison between the electrophysiological signals corresponding to the different linguistic units under test.

in picking up speech ABR signals as electrophysiological signals;

in picking up speech ABR and cortical AEP signals as electrophysiological signals.

The Applicant thus seeks to respond to a clear need that does not have a solution in practice. Neurophysiological discrimination between two acoustically similar language sounds is key in understanding language. Furthermore, the invention makes it possible to test either a single prosthesis (monaural stimulation), or two prostheses one after the other (monaural stimulation, right then left, or vice versa), or indeed two prostheses simultaneously (binaural stimulation, dichotic stimulation). The invention thus makes it possible to optimize the stereo made possible by a bilateral auditory appliance, the mono-stereo made possible by a unilateral appliance in the presence of subnormal contralateral hearing, or the stereophonic hearing resulting from a unilateral appliance in the presence of abnormal contralateral hearing. The neurophysiological signals transmitted by said auditory nervous system in response to the auditory stimulus and recorded by means of an electro- or magneto-encephalography system are referred to below as "electrophysiological signals".

For an individual suffering deafness, the important point is not to comply with normative data, but rather to "recover" hearing or at least to be capable of distinguishing between different linguistic units that make up that individual's language so that the individual can relearn how to understand the language and interact with different speakers.

Electrophysiological measurements make it possible to determine objectively whether the acoustic speech signal is properly transmitted by the auditory prosthesis and processed by the sub-cortical and cortical auditory channels. For this purpose, the invention makes it possible to pick up separately or simultaneously the responses of the brainstem, also referred to as sub-cortical responses ("speech Auditory Brainstem Responses" referred to herein as "speech ABRs"), and cortical responses (cortical Auditory Evoked Potentials referred to below as cortical "AEPs") to speech sounds amplified by the auditory prosthesis. These measurements are picked up from a patient wearing the hearing aid in an ecological listening situation, i.e. via the patient's own auditory hearing aids or those that might be acquired. The responses evoked by speech sounds, in detail, are as follows:

at sub-cortical level, a transient impulse response (onset response), triggered by the beginning of the stimulus and similar to the brainstem responses to a transient stimulus of click type, followed by a frequency following response (FFR), which is described as representing the composite neuronal activity of the brainstem synchronized with the periodicity of the stimulus; and at cortical level, a succession of waves that are slower than those generated at sub-cortical level, in particular on front central electrodes (wave P50 followed by the N1-P2-N2 complex that is also known as N100-P200-N200), and on the temporal electrodes (T complex).

Until now:

speech ABR has been picked up from subjects having hearing aids only when their ears are bare (i.e. after removing the prostheses), and never while administering speech sounds via the auditory prosthesis; and simultaneous recording of speech ABRs and cortical AEPs has not been proposed for wearers of hearing aids.

In a particular implementation, the method consists in comparing the electrophysiological signals corresponding to the various tested linguistic units by performing one or more of the following steps consisting:

in extracting peak latencies, peak amplitudes, latency differences between peaks, slopes of the curve between two peaks, or areas under portions of the curve;

in searching in waveforms and/or in time-frequency decompositions for a response specifically expected for one of said linguistic units;

in directly comparing the waveforms of each neurophysiological signal picked up in response, e.g. by subtraction; and in comparing the time-frequency decompositions.

The advantage of performing these various steps lies in the fact that they are easily done by any person familiar with signal processing. These comparisons are performed after processing the raw signal, which processing includes one or more of the following steps: rejecting and/or correcting artifacts, filtering the signal, averaging all of the signals in response to presentations of the same stimulus, and transferring from the time domain to the spectral domain. These are conventional steps that constitute the basis for signal processing in human electrophysiology. It is possible also to add advanced methods of de-noising signals and/or separating sources, such as principal component analysis or independent component analysis, known to the person skilled in the art.

In a preferred implementation, the method consists in selecting the linguistic units from phonemes, tonemes, or chronemes, or assemblies thereof as syllables.

The advantage of selecting the linguistic units from phonemes, tonemes, or chronemes lies in the fact that these cover all spoken languages. Linguistic units differ from one another by different acoustic traits. Examples of acoustic traits making it possible to discriminate between phonemes in French are: either a frequency content of low/high, compact/diffuse, or oral/nasal type, or a time characteristic of continuous/discontinuous, vowel/non-vowel, or voiced/non-voiced type, or indeed a combination of these traits.

In tone languages, such as Mandarin Chinese, it is possible to use characters or words as linguistic units, each character possibly being constituted: by an initial portion such as a consonant and by a final portion such as a vowel.

The monosyllabic words also referred to as "characters" are constituted by an initial portion and a final portion and they are differentiated by tone variations. For example, four tone variations are used in Mandarin Chinese for the vowel /a/:

ā, a stable tone throughout the pronunciation of /a/;
á, a tone that rises between the beginning and the end of pronunciation /a/;
à, a tone that falls between the beginning and the end of pronunciation /a/; and
ǎ, a tone that falls at the beginning of pronunciation and then rises again at the end of pronunciation.

In a preferred implementation, the method consists in selecting linguistic units from minimal pairs (two phonemes that are distinguished by a single acoustic trait), in particular from a phonetic confusion matrix.

In a preferred implementation, as a function of the result of said processing of the signals, the method consists in identifying at least one acoustic trait of said stimulus for which the processing by said auditory nervous system is insufficient to enable said neurophysiological discrimination of said transmitted linguistic units.

In a preferred implementation, the method consists in changing at least one adjustment parameter of said auditory prosthesis as a function of said acoustic trait that is processed by said auditory nervous system insufficiently to enable said neurophysiological discrimination of said transmitted linguistic units.

In a preferred implementation, the method consists in transmitting the stimulus to a prosthesis via a wireless link.

Various other characteristics appear from the following description made with reference to the accompanying drawings, which show implementations of the invention as non-limiting examples:

FIG. 1 is a diagram of an experimental setup for performing the present invention.

FIGS. 2A, 2B, 2C, and 2D show respectively an auditory stimulus constituted by the linguistic unit /ta/, its transmission by means of an insert type earphone, a speech ABR measurement, and a cortical AEP measurement.

FIGS. 2E, 2F, 2G, and 2H show respectively an auditory stimulus constituted by the linguistic unit /ta/, its transmission by means of a BTE-type prosthesis, a speech ABR measurement, and a cortical AEP measurement.

FIGS. 3A, 3B, 3C, and 3D show respectively an auditory stimulus constituted by the linguistic unit /da/, its transmission by means of an insert type earphone, a speech ABR measurement, and a cortical AEP measurement.

FIGS. 3E, 3F, 3G, and 3H show respectively an auditory stimulus constituted by the linguistic unit /ta/, its transmission by means of a BTE-type prosthesis, a speech ABR measurement, and a cortical AEP measurement.

FIGS. 4A, 4B, and 4C show steps in performing the present invention by subtracting neurophysiological measurements obtained for the two linguistic units /da/ and /ta/ presented by means of a BTE-type prosthesis.

FIG. 5 shows a confusion matrix in English.

FIG. 6 shows the characteristic frequency contents of each consonant in French (phonetic frequency chart).

Figure 1:
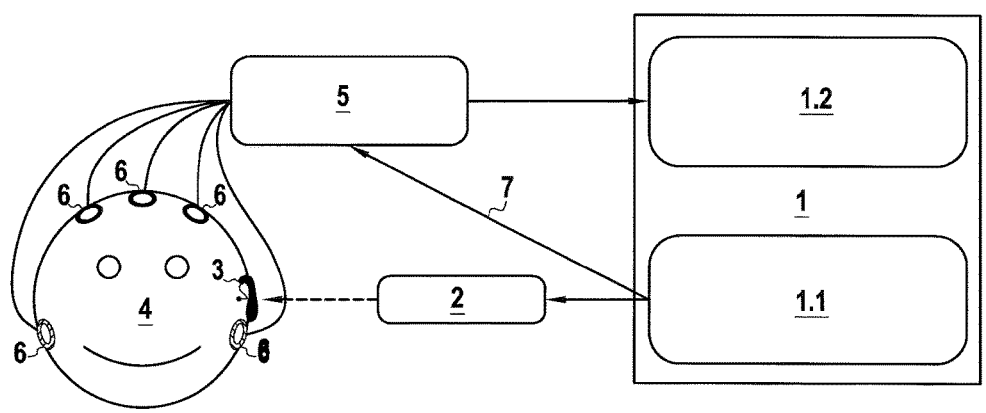

FIG. 1 shows an experimental setup for performing the invention. By way of illustration, such a setup comprises a central unit 1 such as a computer having firstly a control module 1.1 and secondly a data recorder module 1.2. The device may comprise two separate computers, a first computer including the control module 1.1 and a second computer including the data recorder module 1.2.

In particular, the control module 1.1 of the central unit 1 is connected to a transmitter 2 suitable for transmitting control signals to an auditory prosthesis 3. The auditory prosthesis 3 may be of the external auditory prosthesis type: traditional BTE, slim-tubing BTE, RIC hearing aids, intra-auricular hearing aids, spectacle hearing aids, or indeed prostheses that are totally or partially implanted: bone anchored implants, middle ear implants that are semi- or totally implantable (with air conduction or bone conduction), cochlear implants, electro-acoustic cochlear implants, brainstem implants. Signals may be transmitted between the transmitter 2 and the auditory prosthesis 3 over a wire type connection or a wireless type connection, i.e. by radio transmission (frequency modulation), digital transmission (e.g. Bluetooth®), or any type of transmission by means of electromagnetic waves. The auditory prosthesis 3 is designed to be worn by an individual 4. Thus, the central unit 1 enables an auditory stimulus to be transmitted to the auditory nervous system of the individual 4 via the auditory prosthesis 3.

Furthermore, the central unit 1 is connected to an electro- or magneto-encephalographic amplifier 5 (referred to below as an EG amplifier). This EG amplifier 5 is connected to electro-encephalographic electrodes or to magneto-encephalographic sensors 6 arranged in contact with or in the proximity of the head of the individual 4. These electrodes or sensors 6 are adapted to measure or pick up the specific electrophysiological activity in the auditory central nervous system of the individual 4. Thus, the central unit 1 can record this speech ABR type specific electrophysiological activity or the response of the brainstem to a speech sound, or it can record cortical AEP type specific electrophysiological activity (responses of the cerebral cortex to a speech sound).

Finally, the central unit 1 is adapted to synchronize the recording of the electrophysiological activity received via the EG amplifier 5 with the transmitted auditory stimulus by means of a synchronization connection 7 between the control module 1.1 and the EG amplifier 5.

In particular, in the invention, the transmitted auditory stimulus is of the type comprising a pair of linguistic units selected from a phonetic confusion matrix. The term "linguistic unit" is used to mean a phoneme, a toneme, or a chroneme, or indeed an assembly of them making up a syllable. For example, assembling the phoneme /t/ with the phoneme /a/ results in the consonant-vowel type syllable /ta/. Phonemes, tonemes, and chronemes are known as the basic units of phonetics, and they enable all the words that make up languages to be constituted. Confusion matrices are known in phonology and they depend on the language (FIGS. 5 and 6). They have been described in the literature both for French (F. Lefevre, "Impact de la perte auditive sur la perception de la parole: confusions phonétiques" [Impact of hearing loss on speech perception: phonetic confusions], published in Précis d'Audioprothèse, Production, phonétique acoustique et perception de la parole, Elsevier Masson, 2008 (pp. 389-399) and for English (G. A. Miller & P. E. Nicely, "An analysis of perceptual confusions among some English consonants", Journal of the Acoustical Society of America, 1954, 27 (2), pp. 338-352).

In French, in order to compare two linguistic units, it may suffice to select two phonetically similar consonants, pronounced with the same vowel, e.g. the syllables /ta/ and /da/.

The person skilled in the art knows how to insert an insert into the auditory canal of an individual in order to measure specific electrophysiological activity. The term "insert" is used to mean an intra-auricular earpiece constituted by a plastic tube filled with air serving to transmit soundwaves and a foam plug enabling it to be fitted to the diameter of the outer auditory canal. In general manner, the person skilled in the art does not use a prosthesis instead of the insert since there is a prejudice that it is not possible under such conditions to take measurements of the electrophysiological activity of the brainstem.

FIGS. 2A to 2H show the possibility of using auditory prostheses instead of inserts for taking measurements of electrophysiological activity in response to stimuli administered via the auditory prosthesis.

The syllable /ta/ has been tested by means of inserts (FIGS. 2A to 2D) and by means of auditory prostheses (FIGS. 2E to 2H).

Figure 2A:
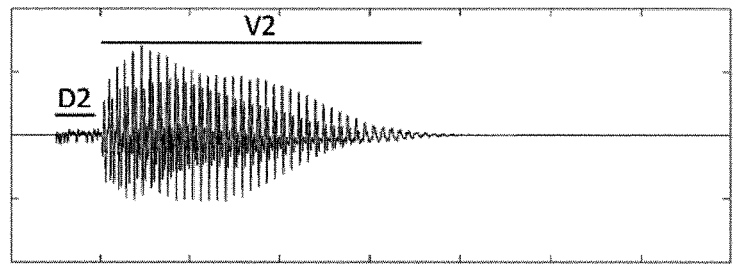
Figure 2B:
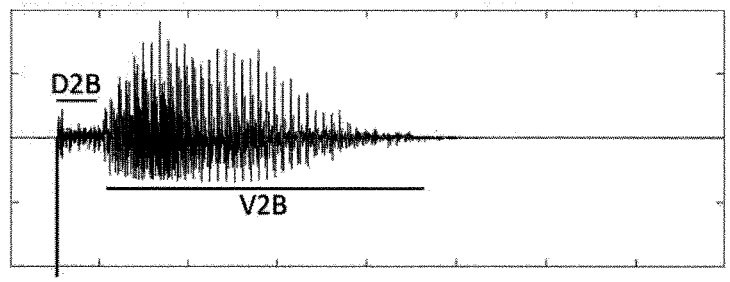
Figure 2C:
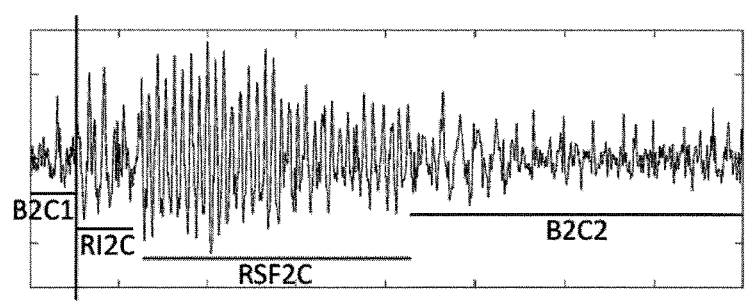
Figure 2D:
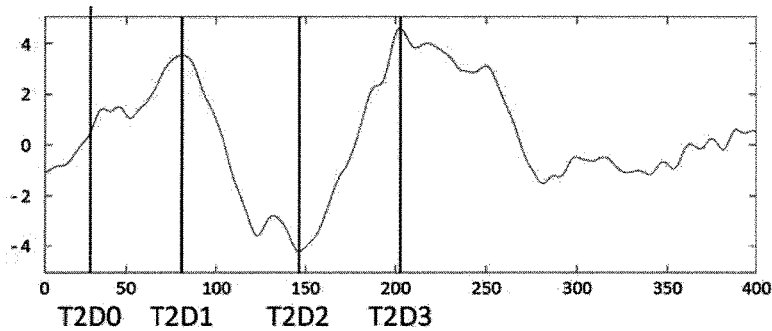
Figure 2E:
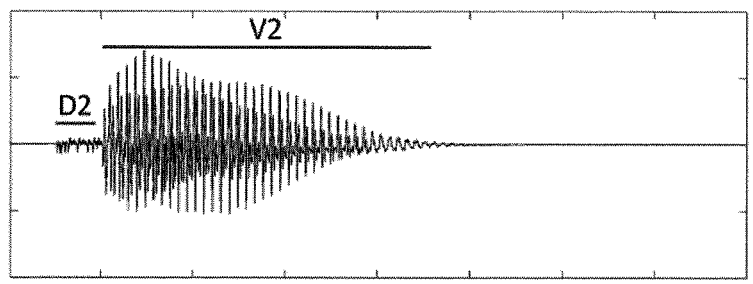

In FIG. 2A, as in FIG. 2E, the syllable /ta/ is shown as transmitted by the control module 1.1 to the central unit 1. In particular, this syllable begins with a transient deocclusion portion corresponding to the expulsion of air contained in the oral cavity as a result of the tip of the tongue being retracted from the top incisors. The deocclusion and the setting into vibration of the vocal chords in order to produce the vowel /a/ are separated by 25 milliseconds (ms), and form the boundaries of the zone D2 that can be considered as the consonant /t/ (including therein the deocclusion and excluding the setting into vibration of the vocal chords). This deocclusion D2 is followed by a zone V2 corresponding to the vowel /a/ for a duration of 200 ms. The zone D2 has a pseudo-period, i.e. undulations of the same period but of varying amplitudes. In particular, in this example the pseudo-period has a duration of 4.6 ms (corresponding to a fundamental frequency of 218 Hz).

As shown in FIG. 2B, the syllable transmitted by the insert has a structure comparable to that of FIG. 2A. The syllable of FIG. 2B has a zone D2B for the consonant /t/ of duration 25 ms followed by a zone V2B for the vowel /a/ of duration 200 ms. The zone V2B has substantially the same duration as the zone V2 and has the same pseudo-period. The vowel re-transmitted by the insert is quite close to the signal sent: in contrast, the consonant—and more particularly the deocclusion—is very distorted: this results in a large peak at the very beginning of the signal output by the inserts, which is very different from the signal as sent. This deformation can be attributed to the flexible plastics material tubes of the inserts, which have a known distortion effect on acoustic signals.

Figure 2F:
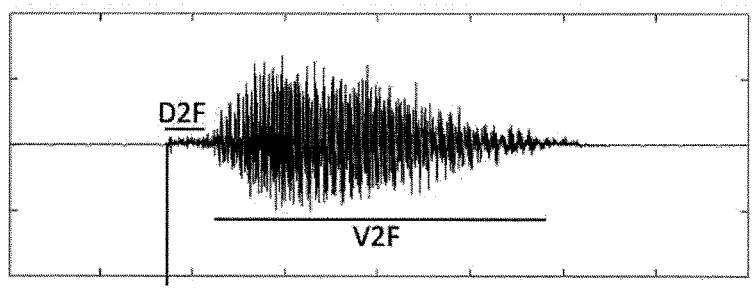

FIG. 2F shows the sound of the syllable /ta/ as transmitted by the auditory prosthesis 3. It can be seen in particular that there is a time offset of 67 ms between the transmission of the syllable by the control module 1.1 of the central unit 1, whereas the time offset due to the insert is negligible (less than 1 ms with flexible plastics tubes having a length of 30 centimeters (cm) and a speed of sound in air of 340 meters per second (m/s)).

Furthermore, the syllable shown in FIG. 2F also has a structure comparable to the structure of FIGS. 2A and 2E. Specifically, this structure comprises in particular a consonant zone D2F and a vowel zone V2F. The consonant is close to the signal as sent, but this time there can be seen frequency distortion of the vowel. The transmitted signal nevertheless depends on the characteristics of the prosthesis and on the adjustments that it has been decided to apply thereto.

Figure 2G:
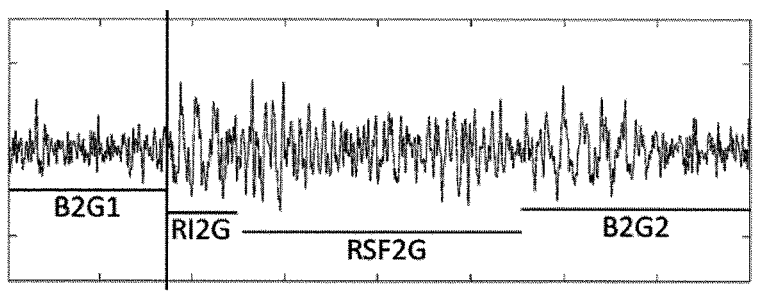

FIGS. 2C and 2G show respectively the speech ABRs measured after transmitting the syllable /ta/ by the inserts and the auditory prostheses 3. These speech ABR type specific electrophysiological activity measurements were acquired with an "actiCHamp" system (from "BrainProducts") having active electrodes, with a sampling frequency of 25 kilohertz (kHz), and with stimulation at a rate of three linguistic units per second (binaural stimulation, i.e. both ears simultaneously). The polarity of the auditory stimulations was alternated in order to be able to use averaging to eliminate possible stimulation artifacts in the electrophysiological responses. The data was recorded at the Cz electrode (placed at the vertex), referenced to the average of two pickup electrodes placed on the mastoids. The speech ABRs were obtained from 3000 individual tests, with rejection of artifacts, averaging of tests that did not present artifacts, and bandpass filtering in the range 80 Hz to 1000 Hz.

FIG. 2C has two noise zones B2C1 and B2C2, an impulse response RI2C, and a frequency following response zone RSF2C. The impulse response RI2C can be detected firstly because its amplitude is greater than that of the noise B2C, and secondly because it is situated with a latency of about 6 ms after the deocclusion from which this response originates, which corresponds to the time taken by auditory information to arrive in the top portion of the brainstem. The frequency following response zone RSF2C can be detected by the fact that it lasts for about as long (200 ms) as the zone V2B that forms the vowel of the syllable. Furthermore, the signal as picked up has a pseudo-period that is identical to the pseudo-period of the signal as transmitted by the insert: this is the frequency following response (FFR) of periodicity that closely matches that of the periodic signal that gave rise to it.

In the same manner, FIG. 2G includes two noise zones B2G1 and B2G2, an impulse response RI2G, and a frequency following response zone RSF2G. The impulse response RI2G can be detected firstly because its amplitude is greater than that of the noise B2G, and secondly because it is situated at a latency of about 6 ms after the deocclusion from which this response originates, which corresponds to the time taken by auditory information to reach the upper brainstem. The frequency following response zone RSF2G can be detected by the fact that it lasts for about the same length of time (200 ms) as the zone V2F that forms the vowel of the syllable. Once more, the signal as picked up has a pseudo-period that is identical to the pseudo-period of the signal transmitted by the auditory prosthesis 3: this is the frequency following response (FFR) of periodicity that closely follows the periodicity of the periodic signal that gave rise to it.

Figure 2H:
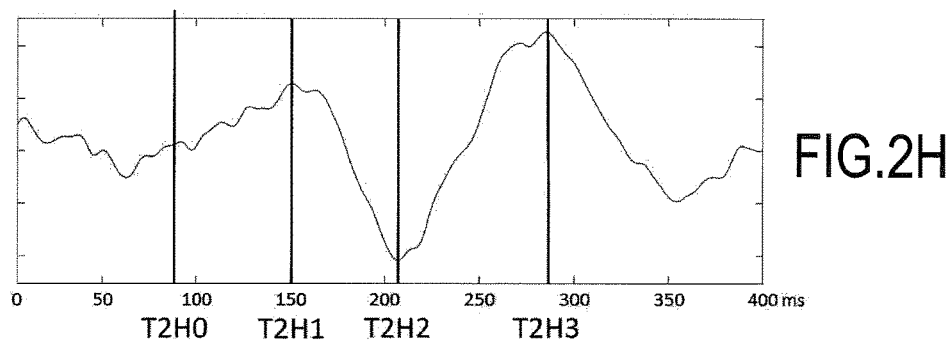

Finally, FIGS. 2D and 2H show respective cortical AEP curves measured after transmitting the syllable /ta/ via the inserts and the auditory prostheses 3. These measurements of cortical AEP specific electrophysiological activity were acquired with a BrainAmp system (from BrainProducts)

having active electrodes (actiCAP), at a sampling frequency of 5 kHz, and with a stimulation rate of one syllable per second. The measurements were recorded at the Cz electrode (placed at the vertex), referenced to the mean of two pick-up electrodes placed on the mastoids. The cortical responses were obtained from 200 individual tests (binaural stimulation, alternating polarities), with artifacts being rejected, averaging, and bandpass filtering in the range 3 Hz to 80 Hz.

The beginning of signal emission from the inserts is referenced T2D0 and the beginning of signal emission from the prostheses 3 is referenced T2H0. The curves present prominent responses referenced at times T2D1, T2D2, and T2D3, and also at times T2H1, T2H2, and T2H3. The various peaks characteristic of the cortical response to the syllable /ta/ shown in FIGS. 2A and 2E are thus present at instants that are substantially identical in comparison with the beginning of signal transmission by the inserts or by the auditory prosthesis:

$$T2H1=T2D1+(T2H0-2D0)=T2D1+67 \text{ ms}$$

More precisely, each transient event, i.e. each rapid change in acoustic energy level, gives rise in the auditory nervous system to a series of at least three waves: P50, N100, and P200, the letter giving the polarity (P for positive and N for negative), and the number giving the latency in milliseconds. Since the syllable /ta/ is made up of a plurality of transient events such as the deocclusion or the setting into vibration of the vocal chords, a corresponding number of series of three waves are evoked in the central auditory nervous system, and they are superposed in the cortical AEPs.

The Applicant has thus overcome a prejudice of the person skilled in the art. It is possible to make measurements of speech ABRs and cortical AEPs by using a device that has an auditory prosthesis instead of a conventional insert type earpiece.

The purpose of the method of the invention is to evaluate the effectiveness of the prosthesis 3 in the sense that proper adjustment of the prosthesis should assist the individual 4 in discriminating or distinguishing between linguistic units selected from the confusion matrix. The understanding of speech by the individual 4 relies on the individual's ability to discern the various phonemes of the language used; this is where the various possible adjustments of the prosthesis 3 play a crucial role.

The method of the invention consists in transmitting an auditory stimulus to the auditory central nervous system of the individual 4 via the prosthesis 3. This stimulus is made up of at least one pair of linguistic units selected from a phonetic confusion matrix. The method then consists in using the data recorder module 1.2 of the central unit 1 to pick up the neurophysiological signals generated in said auditory central nervous system in response to the auditory stimulus for each linguistic unit by means of the electrodes 6 and the EG amplifier 5. The received signals are then processed separately for each of the linguistic units and then at least one of the parameters of the electrophysiological responses to these two linguistic units are compared in order to test whether or not the auditory central nervous system exhibits any neurophysiological discrimination between the various units, with the effectiveness of the auditory prosthesis being evaluated on the basis of the result of this comparison.

In practice, the stimulation is repeated a number N of times lying in the range 100 to 6000, preferably in the range 1000 to 2000 for sub-cortical responses, and at least 100 for cortical responses. By way of example, the two linguistic units are transmitted the same number of times each, i.e. N times each. The linguistic units are preferably transmitted randomly, and with alternating polarities in order to minimize stimulation artifacts, if any.

FIGS. 3A to 3H and 4A to 4C show an example of the method of the invention being performed to compare the linguistic units /ta/ and /da/.

Figure 3A:
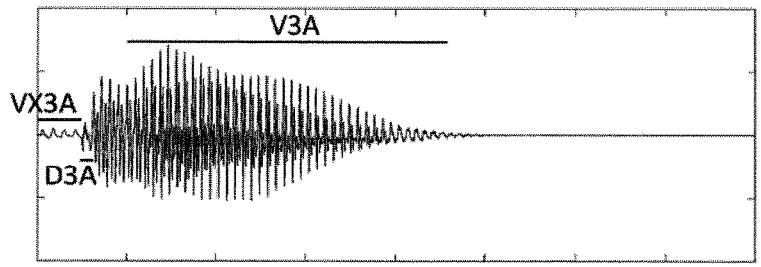
Figure 3B:
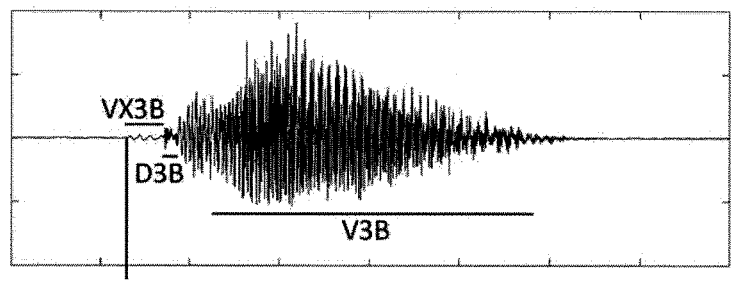

FIG. 3A shows the signal of the sound /da/ as transmitted by the control module 1.1 of the central unit 1, and FIG. 3B shows the signal of the sound /da/ as recorded at the output from the auditory prosthesis 3. In particular, this syllable begins with a respective zone VX3A or VX3B of voicing for a duration of 25 ms, i.e. of vibration of the vocal chords during the occlusion that is specific to the phoneme /d/; followed by a respective deocclusion D3A or D3B having a duration of 5 ms. The consonant /d/ is thus constituted by the following elements: voicing (setting the vocal chords into vibration), deocclusion (withdrawing the tip of the tongue from the top incisors), followed by very rapid return to voicing, which constitutes the beginning of the vowel /a/. This deocclusion D3A or D3B is followed by a zone V3A or V3B of the vowel /a/ of duration 200 ms, having a pseudo-period of duration 4.6 ms.

Figure 3C:
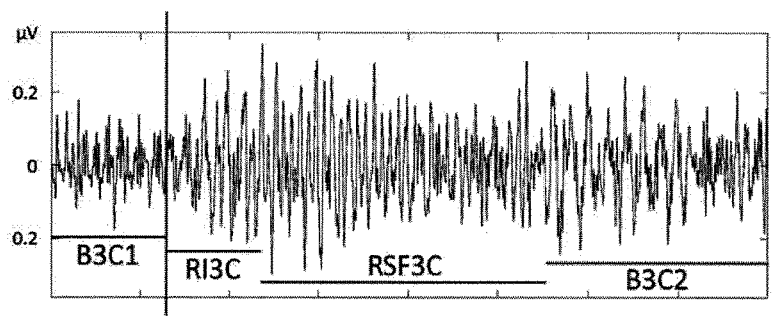

FIG. 3C shows the speech ABRs measured after transmitting the syllable /da/ by the auditory prostheses 3. The curve has two noise zones B3C1 and B3C2, an impulse response RI3C, and a frequency following response zone RSF3C. The impulse response RI3C can be detected firstly because its amplitude is greater than that of the noise B3C, and secondly because the zone RI3C coincides in time with the deocclusion zone D3B, i.e. immediately after the beginning of the sound stimulation (the voicing). The frequency following response zone RSF3C is detected by the fact that it has the same duration of 200 ms as the vowel V3B. Furthermore, the undulations have a pseudo-period closely following the pseudo-period of the signal transmitted by the auditory prosthesis 3.

Figure 3D:
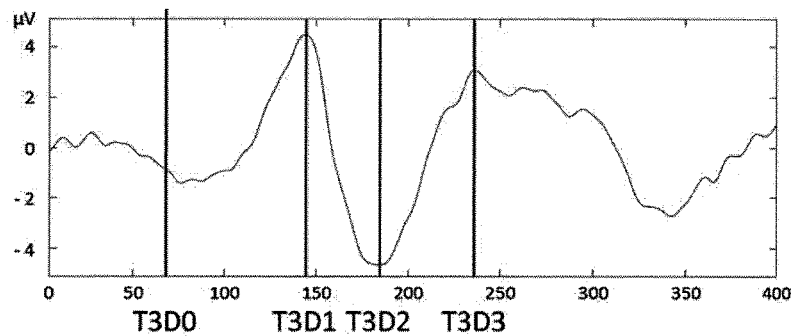

The beginning of the emission of the signal of the sound /da/ is written T3D0 for the emission time of the deocclusion. The curve of the cortical AEPs for the syllable/da/as presented via the auditory prostheses 3, and as shown in FIG. 3D, presents prominent responses marked at the times T3D1, T3D2, and T3D3, corresponding to the P50, N100, and P200 waves.

Figure 3E:
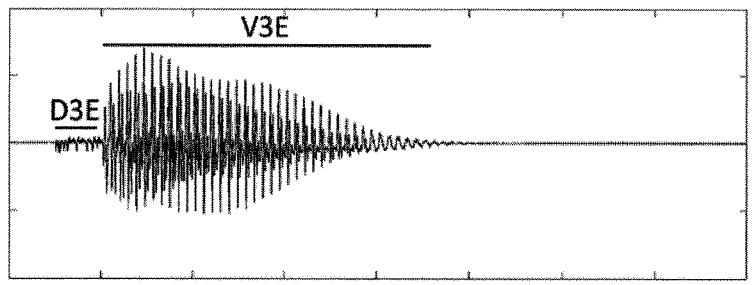
Figure 3F:
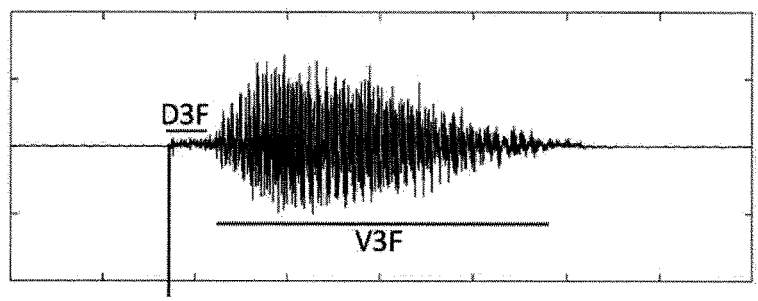

FIG. 3E shows the signal of the sound /ta/ as transmitted by the control module 1.1 of the central unit 1, and FIG. 3F shows the signal of the sound /ta/ as recorded at the output from the auditory prosthesis 3. In particular, this syllable begins with a zone D3E of deocclusion having a duration of 5 ms, in other words a zone of consonant formation. This deocclusion zone D3E is followed by a vowel zone V3E of duration 200 ms. The zone V3E has a pseudo-period with the same duration as the zone V3A, since it is the same vowel.

Figure 3G:
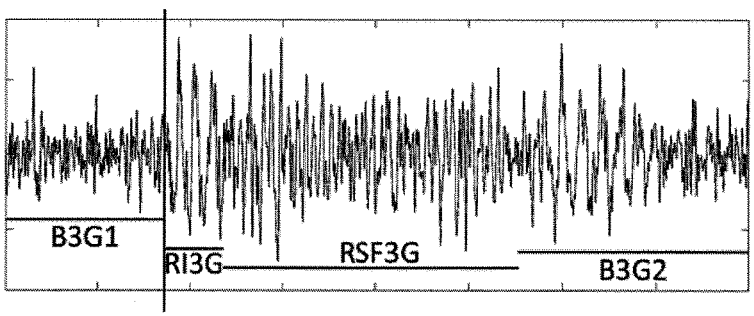

FIG. 3G, which shows the speech ABR for the syllable /ta/ transmitted by the auditory prosthesis 3 has two noise zones B3G1 and B3G2, an impulse response zone RI3G, and a zone RSF3G of frequency following response. The impulse response zone RI3G can be detected because its amplitude is greater than that of the noise B3G1 and B3G2. The frequency following response zone RSF3G can be detected because it has the same duration of 200 ms as the zone V3F that forms the vowel of the syllable. Furthermore, the undulations have a pseudo-period that is the same as the pseudo-period of the signal transmitted by the auditory prosthesis 3.

Figure 3H:
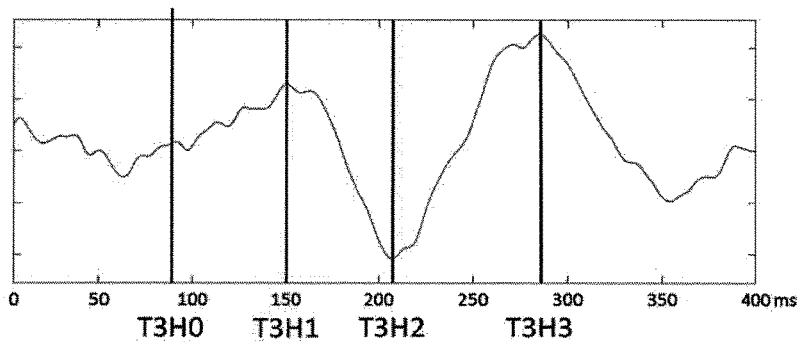

The beginning of the emission of the signal of the sound /ta/ is written T3H0 for the time of the deocclusion. The curve of the cortical AEPs for the syllable /ta/ transmitted by the auditory prostheses 3 is shown in FIG. 3H and presents prominent responses marked at times T3H1, T3H2, and TH3H, corresponding to the P50, N100, and P200 waves.

In order to compare the electrophysiological signals corresponding to the linguistic units /ta/ and /da/, one or more of the following steps may be performed. After the preprocessing step (rejecting artifacts, filtering, averaging, other denoising steps), that serve to obtain the speech ABR and/or the cortical AEP curves, it is possible:

- to extract peak latencies, peak amplitudes, latency differences between peaks, slopes of the curve between two peaks, or the areas under portions of the curve;
- to search in the waveforms and/or in time-frequency decompositions for a response specifically expected for one of said linguistic units;
- to compare the waveforms of each neurophysiological signal picked up in response directly by subtraction; and
- to compare the time-frequency decompositions.

Figure 4A:
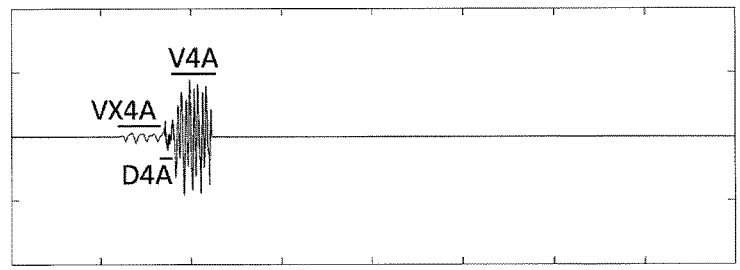

By way of example, in order to compare the waveforms of each signal directly, it is possible to perform subtraction. FIG. 4A shows subtraction between the signals /da/ and /ta/ as delivered by the computer 1 via the prosthesis 3 to the individual 4, these signals /da/ and /ta/ being shown respectively in FIGS. 3A and 3E. In particular, FIG. 4A shows the acoustic difference between the linguistic units /da/ and /ta/. These differences lie in the initial portion of the linguistic unit: voicing VX4A, deocclusion D4A, and start of the vowel V4A. The frequency composition of the signal changes during the syllable, and the frequency composition at the beginning of the vowel depends on the preceding consonant: this is shown by the zone V4A. In contrast, the vowel is identical in both syllables (V3A and V3F).

Figure 4B:
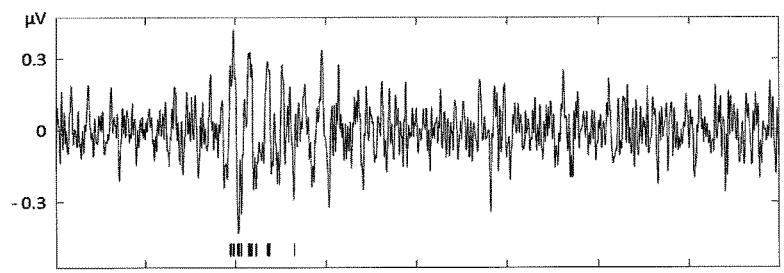
Figure 4C:
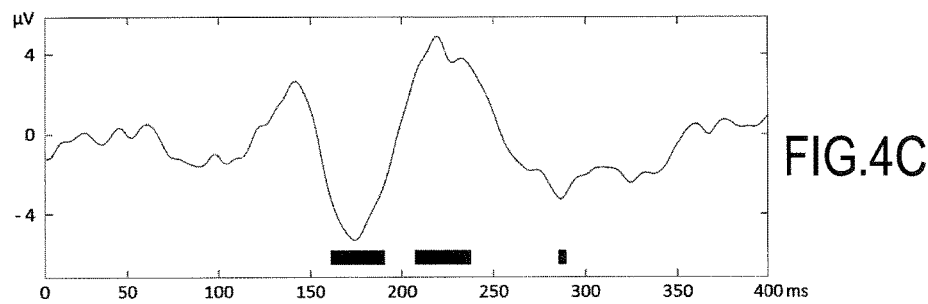

FIG. 4B shows subtraction between the speech ABR measurements as shown in FIGS. 3C and 3G, while FIG. 4C shows subtraction between the cortical AEP measurements as shown in FIGS. 3D and 3H. A Wilcoxon statistical test has been performed on the N repetitions, time sample by time sample, with p<0.05, corrected for multiple tests by false discovery rate (FDR), this statistical procedure making it possible to monitor the rate of "false positives" by means of the set of statistical tests performed (in this example one per time sample, i.e. 10,000 tests for speech ABR, sampled at 25,000 Hz, FIG. 4B, and 2000 tests for cortical AEP, sampled at 5000 Hz, FIG. 4C).

Thus, the time samples for which the electrophysiological signals are significantly different between the two linguistic units are shown up by black bars under the curve. This means that by asserting that these signal zones are different for the two stimuli, there is less than 5% probability of being wrong (for p<0.05).

In particular, FIG. 4B shows the neurophysiological discrimination between the syllables /da/ and /ta/ in the speech ABRs, since statistically significant differences exist between the electrophysiological responses generated by the two linguistic units, as shown by the black bars in the 30 ms following the beginning of the vowel. Likewise, FIG. 4C shows neurophysiological discrimination between the syllables /da/ and /ta/ in the cortical AEPs, since there are differences at latencies corresponding to the waves P50 and N100 evoked by the starts of the sounds. These results indicate that neurophysiological discrimination does indeed exist between /da/ and /ta/, i.e. that the auditory nervous system is appropriately processing differences between the two consonants and in particular the voicing that is present only for/da/. In an implementation of the invention, it is possible to envisage picking up only the speech ABR signals as electrophysiological signals and processing those signals in such a manner as to evaluate in pertinent manner the effectiveness of an auditory prosthesis. In another implementation of the invention, provision may be made to pick up the speech ABR signals and the cortical AEP signals and then to process them in the manner described above.

FIG. 5 shows a phonetic confusion matrix in English and it shows up three particular types of confusion:

- concerning the presence or absence of a final consonant, e.g. "rope" and "row";
- concerning the initial consonant, e.g. "cook" and "took"; and
- concerning the presence or absence of an initial "s", e.g. "ski" and "key".

FIG. 6 is a phonetic frequency chart showing the various frequency zones of each consonant in French. The overlap of these frequency zones explains most phonetic confusions of a subject who is hard of hearing and/or who is using a poorly adjusted auditory prosthesis. The confusions that are the most frequent relate to the following pairs of consonants: /p/-/t/, /k/-/t/, /f/-/s/, /ʃ/-/s/, /b/-/d/, and /m/-/n/.

Finally, the method of the invention for evaluating the effectiveness of an auditory prosthesis makes it possible to change at least one adjustment parameter of said auditory prosthesis. Specifically, for example by using the information of a phonetic frequency chart, it is possible to determine the acoustic trait(s) that is/are processed poorly by said auditory nervous system, and thus to change the adjustment parameters of the auditory prosthesis in order to enable said neurophysiological discrimination to take place between the transmitted linguistic units.

For example, if /da/ and /ta/ are not discriminated between by the individual 4, that means that the individual is not perceiving the difference in voicing, which is due to hearing loss at low frequencies, i.e. for frequencies in the range 100 Hz to 300 Hz. Consequently, the prosthesis parameter for changing is gain in the frequency range 100 Hz to 300 Hz.

In certain kinds of hearing loss, and in particular in presbycusis, hearing at low frequencies is relatively well preserved. That is why low frequencies are usually amplified little or not at all by the auditory prosthesis, so they reach the auditory nervous system solely via such preserved hearing at low frequencies. Nevertheless, it is essential for the auditory nervous system to be able to encode as well as possible all of the spectral components of speech, including low frequencies, so as to enable the user of an auditory prosthesis to understand a speaker. The above-described method of picking up speech ABRs, while delivering speech sounds directly via an auditory prosthesis, relies on administering sound levels that are defined by the adjustment parameters of said auditory prosthesis. A tested subject is thus deprived of naturally hearing low frequencies. By stimulating directly via the prosthesis, the method consequently makes provision for delivering a signal that is enriched at low frequencies compared with the amplification that would otherwise be applied in a natural situation, in order to add to the input signal the acoustic information that would normally arrive in daily listening via the preserved hearing at low frequencies. This methodological precaution formally conditions the transcription of spectral characteristics of speech sounds in the speech ABR signal that is picked up using said method in accordance with the invention.

The invention is not limited to the examples described and shown since various modifications may be applied thereto without going beyond its ambit.

The invention claimed is:

1. A method of evaluating the effectiveness of an auditory prosthesis (3), the method comprising:
    transmitting a stimulus via an auditory prosthesis (3), thereby delivering an auditory stimulus to the auditory nervous system of a person fitted with said auditory prosthesis;
    picking up the neurophysiological signals transmitted by said auditory nervous system in response to the auditory stimulus by means of an electro- or magneto-encephalography system; and
    processing the received neurophysiological signals;
    the method further comprising:
    transmitting a stimulus made up of at least one pair of linguistic units selected from a phonetic confusion matrix;
    picking up separately the electrophysiological signals in response to each linguistic unit administered via the auditory prosthesis (3); and
    processing the neurophysiological and electrophysiological signals:
        by comparing the electrophysiological signals corresponding to the various tested linguistic units by performing one or more of the following steps comprising:
            extracting peak latencies, peak amplitudes, latency differences between peaks, slopes of the curve between two peaks, or areas under portions of the curve;
            searching in waveforms and/or in time-frequency decompositions for a response specifically expected for one of said linguistic units;
            directly comparing the waveforms of each neurophysiological signal picked up in response by subtraction; and
            comparing the time-frequency decompositions; and
        evaluating the effectiveness of the auditory prosthesis on the basis of the result of this comparison between the electrophysiological signals corresponding to the different linguistic units under test,
    wherein the method further comprises picking up speech ABR signals as electrophysiological signals,
    wherein as a function of the result of said processing of the neurophysiological and electrophysiological signals, the method comprising identifying at least one acoustic trait of said stimulus for which the processing by said auditory nervous system is insufficient to enable said neurophysiological discrimination of said transmitted linguistic units, and
    wherein the method further comprises changing at least one adjustment parameter of said auditory prosthesis as a function of said acoustic trait that is processed by said auditory nervous system insufficiently to enable said neurophysiological discrimination of said transmitted linguistic units.

2. A method of evaluating the effectiveness according to claim 1, wherein cortical AEP signals are picked up as electrophysiological signals.

3. A method of evaluating the effectiveness of an auditory prosthesis according to claim 1, wherein the linguistic units are selected from phonemes, tonemes, or chronemes, or assemblies thereof as syllables.

4. A method of evaluating the effectiveness of an auditory prosthesis according to claim 1, wherein the stimulus is transmitted to a prosthesis via a wireless link.

* * * * *